(12) United States Patent
Feine (10) Patent No.: US 6,976,843 B2
(45) Date of Patent: Dec. 20, 2005

(54) DENTAL SCALER ENHANCEMENTS

(76) Inventor: James Feine, P.O. Box 2009, Bellaire, TX (US) 77402-2009

( * ) Notice: Subject to any disclaimer, the term of this patent is extended or adjusted under 35 U.S.C. 154(b) by 261 days.

(21) Appl. No.: 10/065,274

(22) Filed: Sep. 30, 2002

(65) Prior Publication Data

US 2004/0063064 A1 Apr. 1, 2004

(51) Int. Cl.$^7$ .............................. A61C 1/02; A61C 1/07
(52) U.S. Cl. ...................................... 433/101; 433/119
(58) Field of Search ......................... 433/101, 86, 119, 433/118; 601/2; 606/169; 604/22

(56) References Cited

U.S. PATENT DOCUMENTS

| | | | |
|---|---|---|---|
| 4,820,152 A * | 4/1989 | Warrin et al. .................. | 433/86 |
| 5,451,161 A * | 9/1995 | Sharp ........................... | 433/119 |
| 6,164,968 A | 12/2000 | Feine ............................ | 433/119 |
| 6,190,167 B1 * | 2/2001 | Sharp ........................... | 433/119 |
| 6,241,520 B1 * | 6/2001 | Gofman et al. ............... | 433/119 |
| 6,569,109 B2 * | 5/2003 | Sakurai et al. ................ | 601/2 |

FOREIGN PATENT DOCUMENTS

DE  3136028 A1 * 3/1983

* cited by examiner

Primary Examiner—Todd E. Manahan
(74) Attorney, Agent, or Firm—Daniel N. Lundeen; Lundeen & Dickinson, LLP (57) ABSTRACT

An ultrasonic dental scaler automatically supplies a frequency to match a handpiece connecting thereto. A handpiece connector includes one or more passive elements, which affect the resonant frequency produced by the generator. Multiple handpieces, each operating at a different resonant frequency, may thus be used with the same ultrasonic generator. The ultrasonic dental scaler also supports two footswitches. One footswitch includes a foot-controlled power level adjuster. When connected, the footswitch automatically disables the manual power adjuster. Another on-off footswitch includes no power adjustment mechanism. When connected, the manual power adjustment feature of the generator is maintained. Orders for different handpiece frequencies and footswitch types can thus be filled with an inventory of one generator model.

14 Claims, 10 Drawing Sheets

DENTAL SCALER ENHANCEMENTS

BACKGROUND OF INVENTION

This invention relates to dental equipment and, more particularly, to enhancements to dental scaler devices.

Dental work is performed using a variety of tools. Tools such as strippers, forceps, tweezers, pliers, and scalers, are simple and effective for cleaning and maintaining dental work.

Dental scalers, for example, come in a variety of forms. Used to scrape plaque, stains, and bacterial debris from teeth, scalers may include a tip with a curved hook, a hoe-shaped tip, and so on. Some scaler tips are for general surface cleaning, while other tips are useful for particular cleaning jobs, such as scraping near the gum line. In addition to the variety of tip types, tips may also be available in many different sizes.

Manually-operated dental scrapers are common. Recently, however, dental scrapers have entered the realm of high technology. Automatic dental scalers, also know as ultrasonic scalers, for example, automatically resonate a tip connected to an insert in a handpiece at a high frequency to remove plaque from teeth.

The ultrasonic scalers include a generator that electrically causes the scaling tip to vibrate at a very high rate. An alternating current is passed through an induction coil in a handpiece that induces vibration of the magnetostrictive element of an insert in the handpiece. The vibration is transmitted to the tip by a velocity transducer on the end of the magnetostrictive element. The vibration may cause the tip to move elliptically, in a curved linear fashion, or in a "figure eight" pattern.

Because of the high rate of tip vibration, the high-speed ultrasonic scalers generate a significant amount of heat. Accordingly, ultrasonic scalers operate with a water jet in the tip. The water cools the magnetostrictive element and the tip, as well as the tooth being treated, while the scaler operates.

The tip, for example, may vibrate 25,000 times per second (25 KHz). Some tips operate at a lower frequency, while other tips operate at a higher one. If a tip is connected to a generator and handpiece/insert that operate at the improper frequency, the tip does not operate correctly, or can break during operation.

Typically, the generator portion of the ultrasonic scaler produces a single frequency range, to support a single handpiece/insert that operates at that frequency range. To use a handpiece/insert that operates at a different frequency range, a different generator is used. To use handpiece/inserts of different frequencies associated generators for each must be obtained.

Further, given the variety of tip types and sizes, the task of identifying that tips can operate at which frequency ranges may be problematic for the dental professional.

Thus, there is a need to provide an ultrasonic dental scaler that operates at multiple frequencies for multiple handpieces.

SUMMARY OF INVENTION

According to the embodiments described herein, an ultrasonic dental scaler is disclosed comprising a dental generator unit, the dental generator unit comprising circuitry for producing a base resonance signal, and a handpiece connector for coupling a handpiece to the dental generator unit, wherein the ultrasonic dental scaler comprises a passive circuit element which adjusts the base frequency of the resonance signal to a second frequency, matching a resonant frequency of the handpiece.

In one embodiment, the ultrasonic dental scaler further comprises a first potentiometer in the dental generator unit for adjusting the power level of the resonance signal. In a second embodiment, the ultrasonic dental scaler comprises a footswitch connector for coupling a power level controlling footswitch to the dental generator unit, wherein the footswitch connector disables the first potentiometer and couples a second potentiometer in the footswitch to the dental generator unit.

A method is also disclosed in which a handpiece which operates at a resonant frequency is paired with a handpiece connector as a package, wherein the handpiece assembly comprises a passive element which is associated with the resonant frequency; an order from a customer for an ultrasonic dental scaler is taken, the order comprising a first request for a handpiece, wherein the handpiece operates at the resonant frequency; and the package with the dental generator unit is sent to the customer.

In another embodiment, the method further comprises receiving a second request for a footswitch, wherein the second request specifies either a power level control footswitch or an on/off footswitch. The requested footswitch is sent to the customer.

In another embodiment, an inventory of ultrasonic dental scalers with interchangeable handpiece assemblies is disclosed, comprising a plurality of essentially identical generator units comprising circuitry for producing a base resonance signal and a first potentiometer for adjusting the power level of the resonance signal; a plurality of interchangeable handpieces including at least two different sets of assemblies operable at different resonant frequencies, wherein each handpiece includes passive circuitry elements for matching the base resonance signal to the resonant frequency of the handpiece; and first and second sets of footswitches including on/off circuitry, wherein the first set of footswitches enables the first potentiometer and the second set of footswitches disables the first potentiometer and enables a second potentiometer in the second footswitch.

DETAILED DESCRIPTION

Figure 1:
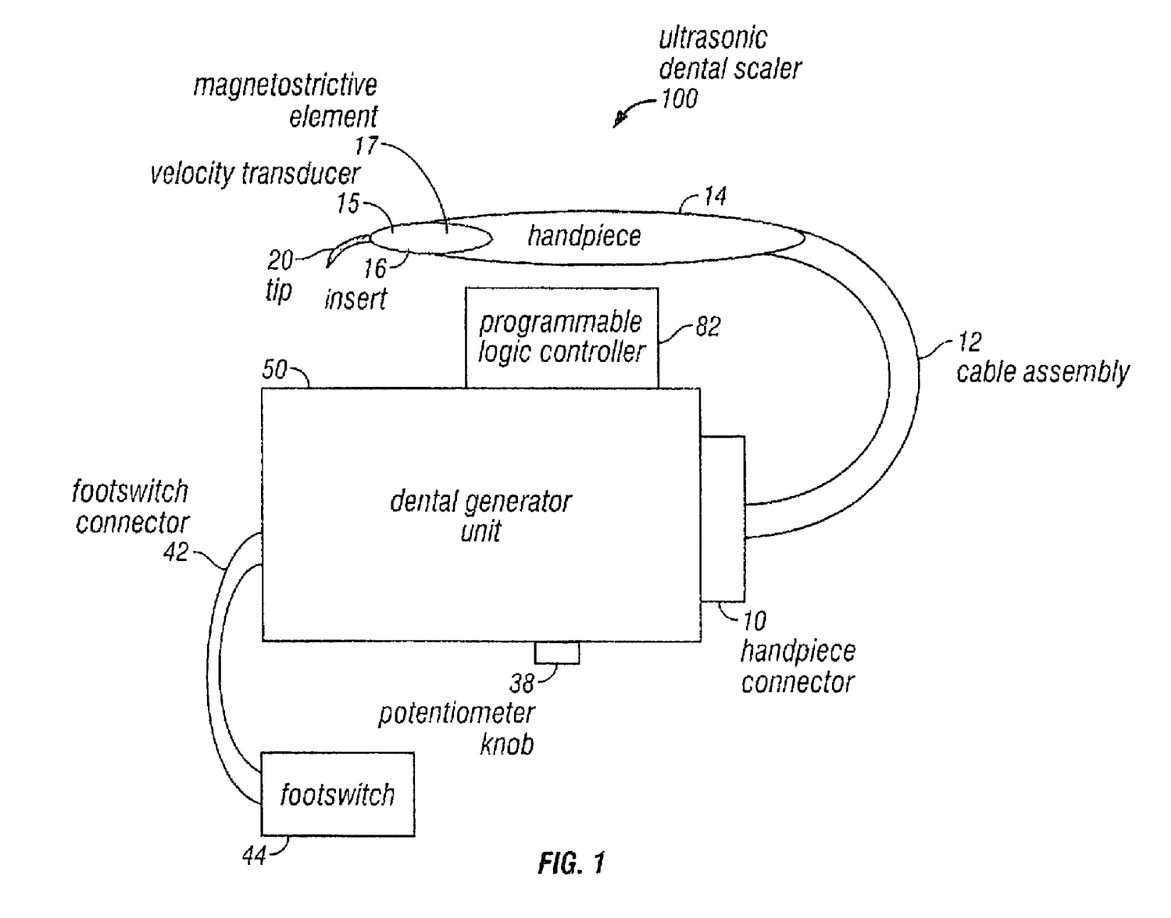
FIG. 1 is a block diagram of an ultrasonic dental scaler according to one embodiment of the invention.

In FIG. 1, according to one embodiment, an ultrasonic dental scaler 100 comprises a dental generator unit 50, a handpiece 14, and a cable assembly 12. A handpiece connector 10 at the end of the cable assembly 12 couples the handpiece 14 to the dental generator unit 50.

The handpiece 14 includes an insert 16, for holding a tip 20. The insert 16 has a magnetostrictive element 17, a velocity transducer 15, and the tip 20. The insert 16 can be a unitary, two-piece, or three-piece assembly, as in U.S. Pat. No. 6,164,968, entitled "Trimodular Ultrasonic Dental Device," which is hereby incorporated by reference as if set forth in its entirety. In one embodiment, the insert 16 may receive many different tips 20 in a variety of shapes. Dental scalers are known to vary by the size and shape of the tip.

The dental generator unit 50 produces a high-frequency resonance signal that passes through the circuitry of the ultrasonic dental scaler 100. This signal produces high-frequency impacts at the insert 16 of the scaler. These impacts are used to remove plaque and other debris from the teeth during cleaning. The ultrasonic dental scaler 100 also includes a footswitch 44, footswitch connector 42, and a programmable logic controller 82. The footswitch and programmable logic controllers are described further, below.

Handpiece: The handpiece 14 and insert 16 can generally be considered conventional in the art. Briefly, the handpiece 14 has a well for receiving the insert 16 about which an inductive coil is disposed for imposing an alternating magnetic field that oscillates the magnetostrictive element 17 at an ultrasonic frequency. The ultrasonic vibrations are transmitted from the magnetostrictive element 17 through the velocity transducer 15 and the tip 20, as is well known in the art. Electrical current from a power supply and control unit (not shown) and water are conventionally supplied to a proximal end of the handpiece 14 via the cable assembly 12.

Each different handpiece 14 is associated with a distinct frequency of operation. Accordingly, each handpiece 14 has its own handpiece connector 10, for coupling the handpiece to the dental generator unit 50.

Figure 2A:
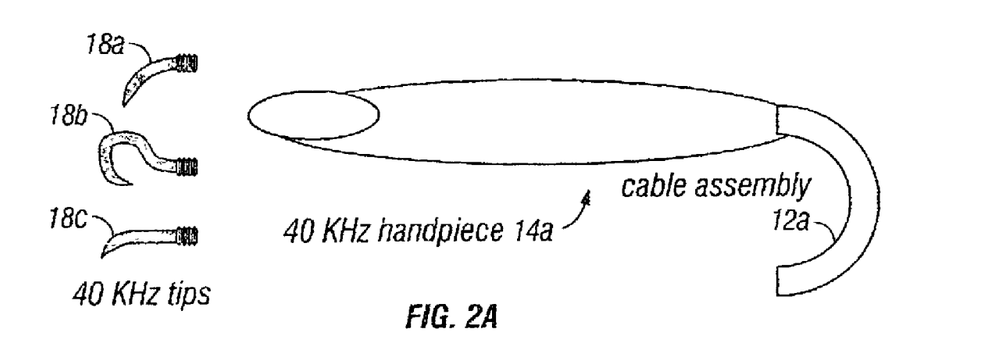
FIGS. 2A–2C are diagrams of handpiece and cable assemblies which operate at three different frequencies according to one embodiment of the invention.
Figure 2B:
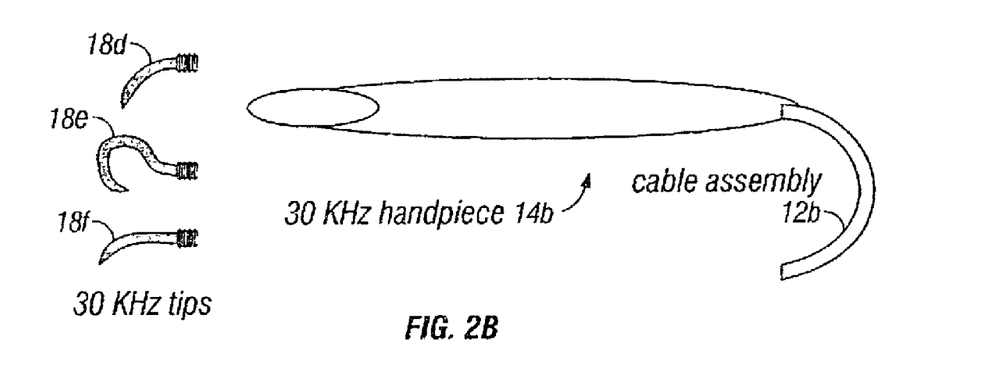
Figure 2C:
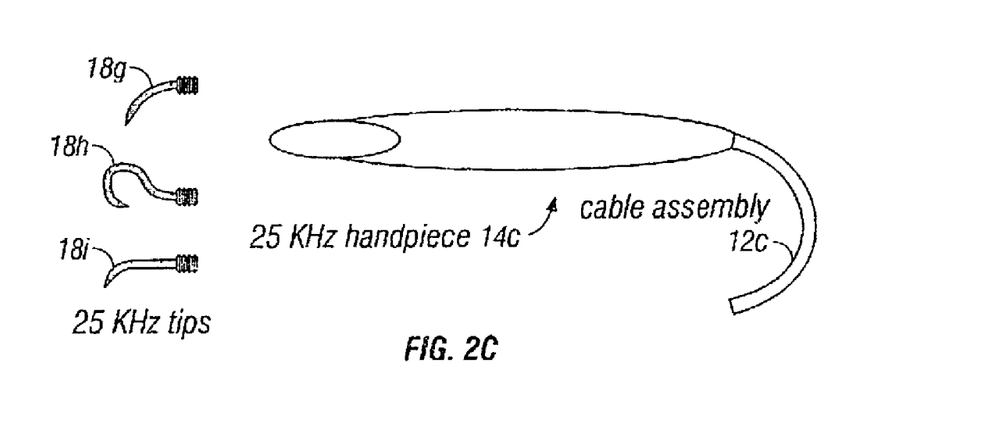

In FIGS. 2A–2C, for example, three handpieces are associated with three different operating frequencies. A handpiece 14a (FIG. 2A) has a resonant frequency of 40 KHz. A different handpiece 14b (FIG. 2B) has a resonant frequency of 30 KHz. A still different handpiece 14c (FIG. 2C) has a resonant frequency of 25 KHz.

Each handpiece 14 has a distinct cable assembly 12 associated therewith, according to one embodiment. For example, the handpiece 14a, for 40 KHz operation, is connected to a cable assembly 12a; the handpiece 14b is connected to cable assembly 12b, for 30 KHz operation; and the handpiece 14c is connected to cable assembly 12c, for 25 KHz operation.

Each of the handpieces 14a–14c may utilize different inserts 16 and/or tips 20. For example, the 40 KHz handpiece 14a may receive any of the 40 KHz tips 18a–18c shown in FIG. 2A. Likewise, the 30 KHz handpiece 14b may receive tips 18d–18f while the 25 KHz handpiece 14c may receive tips 18g–18i.

In one embodiment, the dental generator unit 50 may receive any of the three handpieces 14a, 14b, or 14c (as well as cable assemblies 12a, 12b, or 12c, respectively). As will be shown below, the dental generator unit 50 produces a resonant frequency that depends on which handpiece and cable assembly pair is connected to the unit.

By automatically matching the resonant frequency of the dental generator unit 50 to the connected handpiece, the dental professional need not ascertain which generator unit is being used. Instead, distinct handpieces 14, operating at a variety of frequencies, may be used with a single ultrasonic dental scaler 100.

Figure 3:
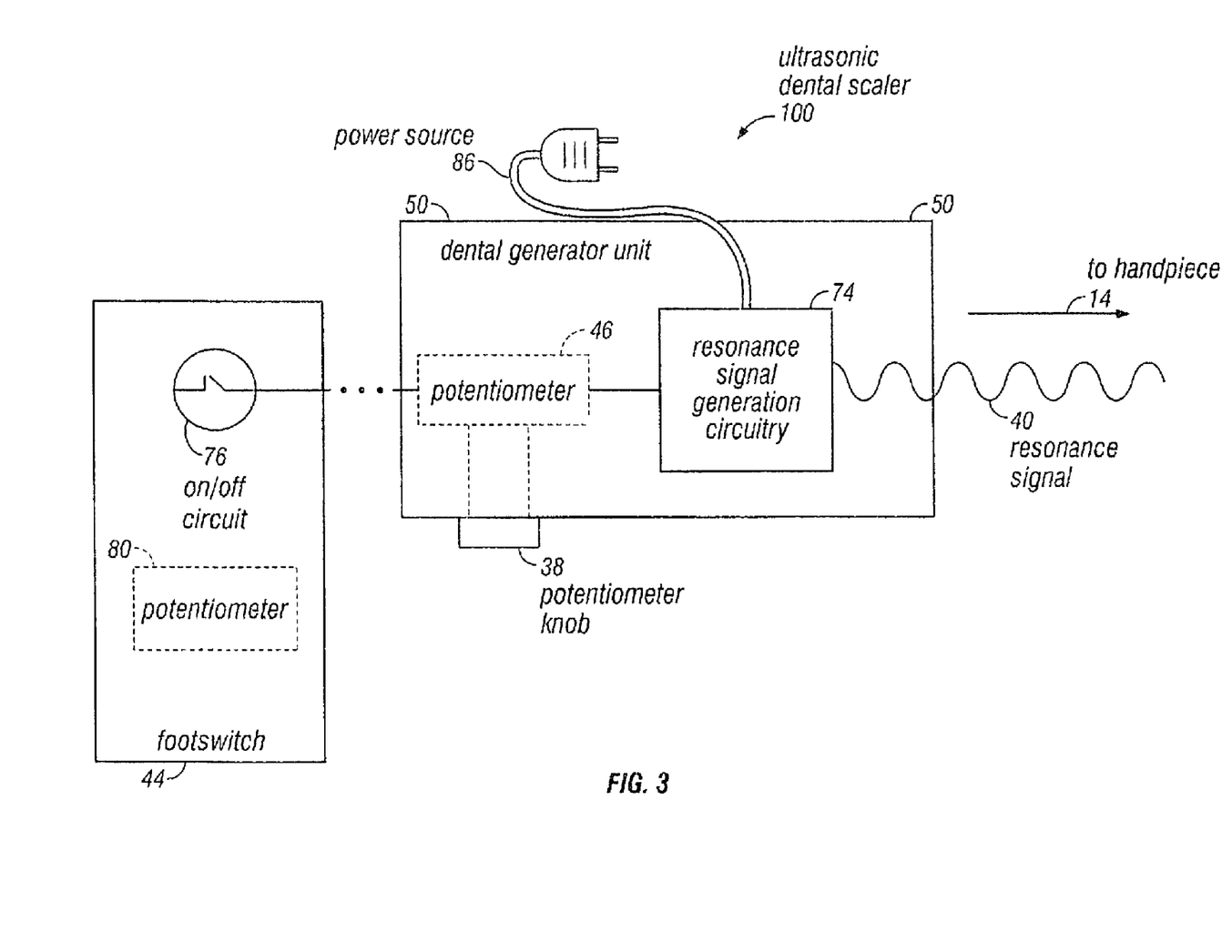
FIG. 3 is a second block diagram of the ultrasonic dental scaler of FIG. 1 according to one embodiment of the invention.

In one embodiment, the dental generator unit 50 includes resonance signal generation circuitry 74, for producing a resonance signal 40 at a base frequency that may be received at the handpiece/insert. As shown in FIG. 3, the dental generator unit 50 also includes a potentiometer 46, for adjusting the power sent to the unit, up or down, within a minimum and a maximum power amount.

In one embodiment, an on/off circuit 76 controls the power sent to the circuitry 74 once a footswitch 44 is connected to the unit 50. Power is received from a power source 86, such as by connecting to a wall outlet supplying electrical power. Alternatively, the dental generator unit can be powered using a battery or other type of power source.

A potentiometer knob 38 that is external to the dental generator unit is shown coupled to a potentiometer 46. A potentiometer is a variable resistor whose resistance is adjustable, such as by turning the knob. The knob 38 controls the magnitude of power supplied to the resonance signal generation circuit 74. Alternatively, a potentiometer 80 within a footswitch 44 may control the power magnitude. Alternative footswitch configurations of the ultrasonic dental scaler 100 are described in more detail, below.

In one embodiment, a coupling of inductors and capacitors produces the resonance signal 40 created in the dental generator unit 50, e.g., an LC circuit, to create a harmonic oscillation of current. Part of the circuit resides within either the handpiece connector 10 or in the handpiece 14.

When the handpiece connector 10 is not coupled to the dental generator unit 50, the LC circuit portion of the generator is not operational, e.g., is open. When the handpiece connector 10 is coupled to the dental generator unit 50, the LC circuit is closed, producing a harmonic oscillation of current. The frequency of the current must match the resonant frequency of the insert 16 in order for the scaler to function properly.

In addition to automatically generating or not generating a resonance signal 40, the ultrasonic dental scaler 100 also automatically determines the proper frequency range for the handpiece 14 that is coupled to the dental generator unit 50. This automatic detection occurs as soon as the handpiece connector 10 is coupled to the unit 50.

Figure 4A:
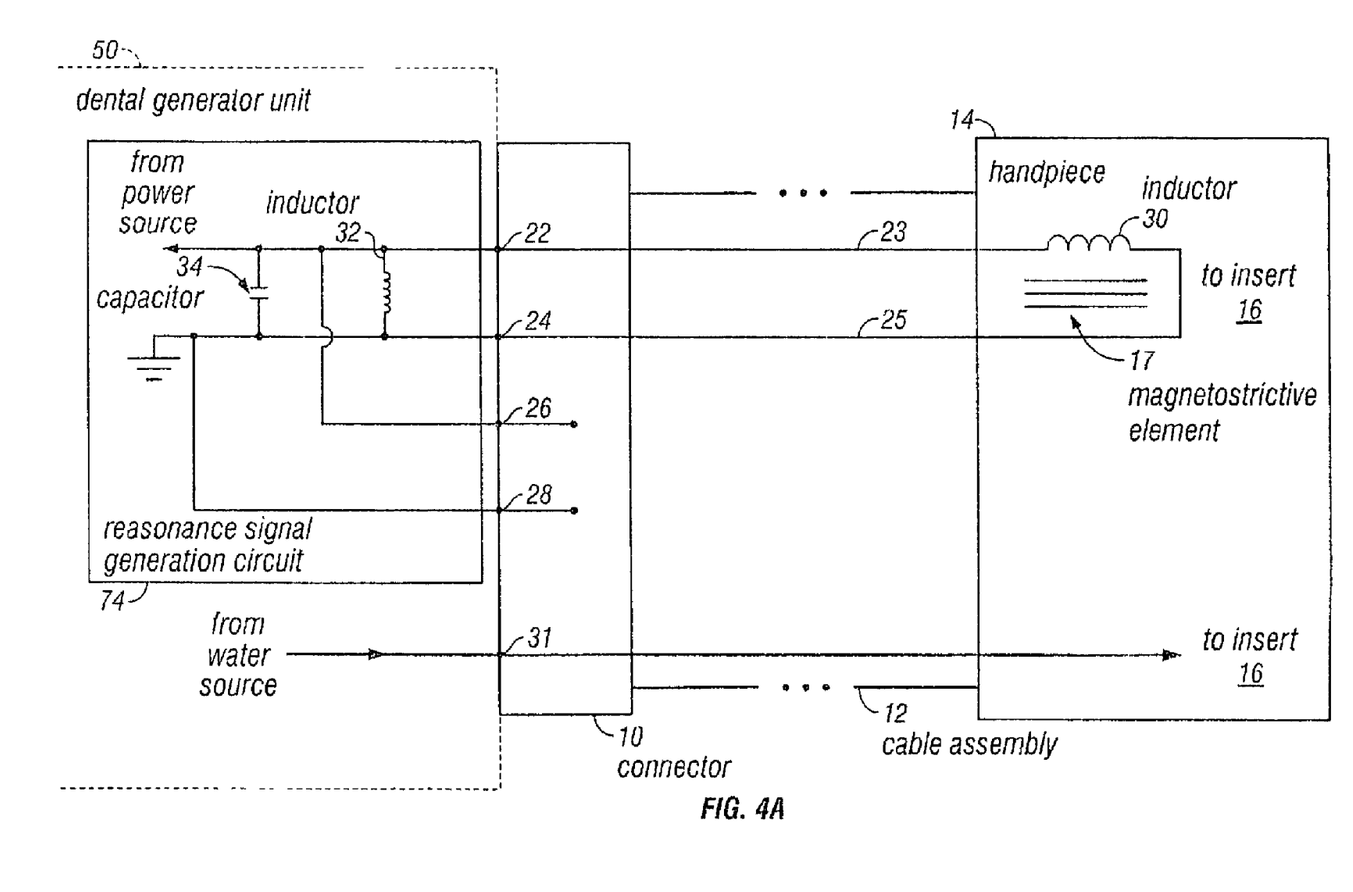
FIGS. 4A–4C are diagrams of the handpiece in association with the dental generator unit according to one embodiment of the invention.
Figure 4B:
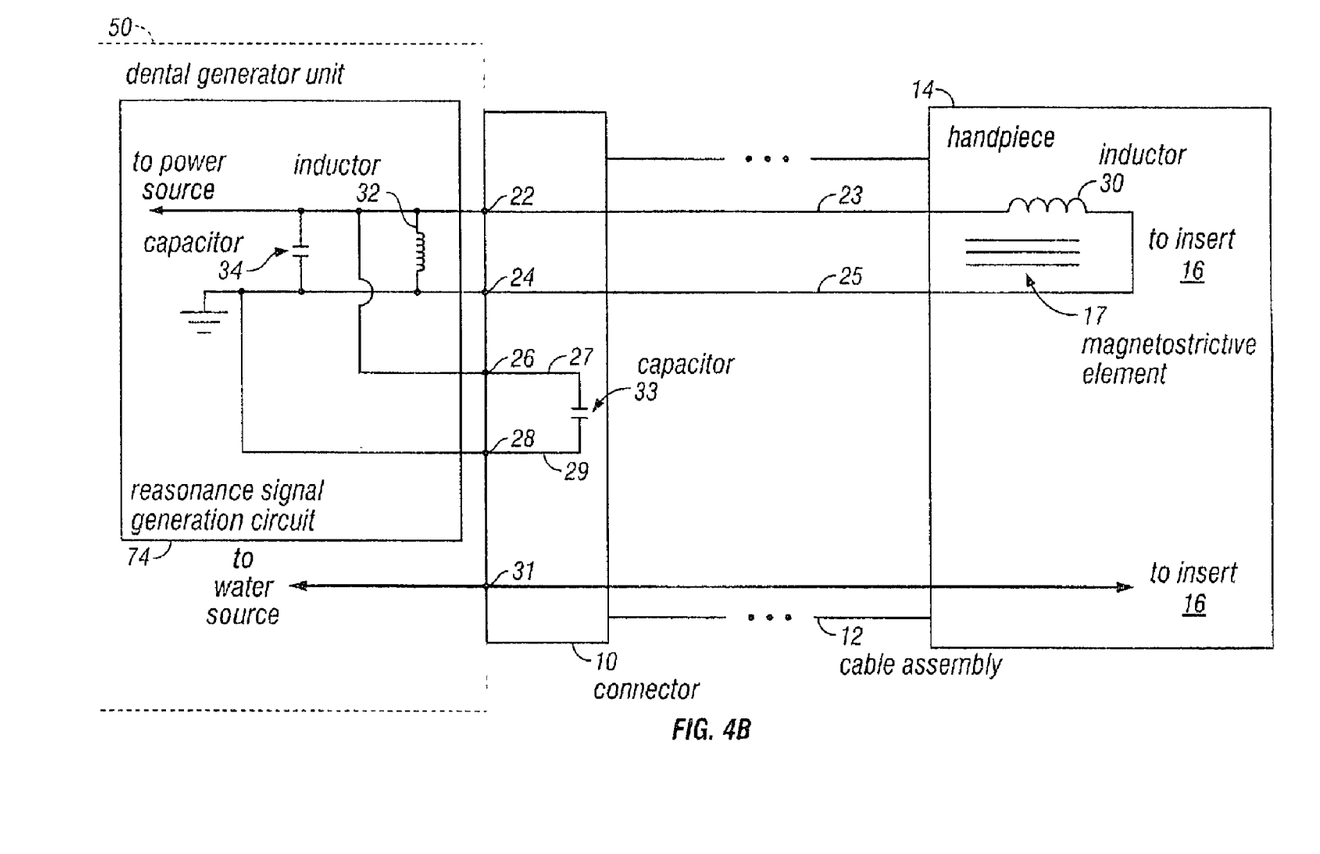
Figure 4C:
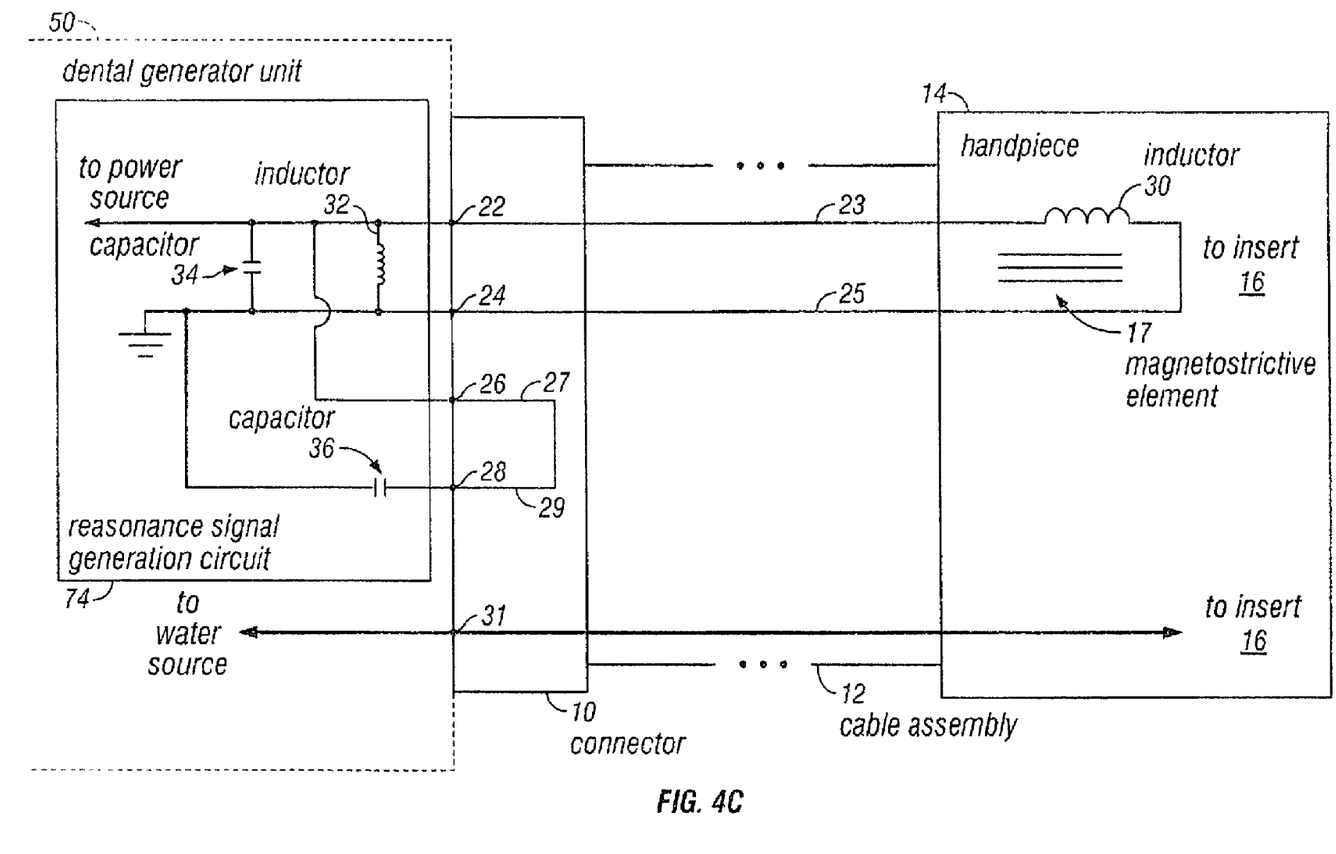

In one embodiment, the handpiece connector 10 is a five-pin connector, as depicted in FIGS. 4A, 4B and 4C. The fifth pin 31 is used as a water port, such that water may flow to the handpiece 14 during use, allowing the instrument to cool during operation while providing lavage.

The other four pins 22, 24, 26, and 28 connect the resonance signal generation circuitry to the handpiece. In FIG. 4A, an inductor 30 is disposed in the handpiece 14, with wires 23 and 25 on either end of the inductor. When the handpiece is connected to the generator 50, wires 23 and 25 connect to the pins 22 and 24, respectively. Accordingly, the inductor 30 in the handpiece is coupled, in parallel, to an inductor 32 and a capacitor 34 within the resonance signal generation circuit 74. Upon receiving a current from a source (not shown), the elements 30, 32, and 34 produce a resonant frequency in the handpiece 14.

The capacitor 34 is of sufficient strength to allow the source signal to resonate at a predetermined frequency. The predetermined frequency may be one of the operating frequencies supported by the ultrasonic dental scaler 100. However, to support additional frequencies, the capacitance may be adjusted.

When capacitors in a circuit are lined up in parallel, their values are added together. A higher capacitance produces a lower resonant frequency 40. Thus, according to one embodiment, additional capacitors are added to the circuit 74 in parallel, in order to lower the operating frequency of the dental generator unit 50.

Capacitors are configured in parallel in various ways. For example, a capacitor is added to the circuit in the handpiece connector 10, as depicted in FIG. 4B, according to one embodiment. A capacitor 33 is disposed in the connector 10 between wires 27 and 29. Wire 27 engages with pin 26 while wire 29 engages with pin 28. Thus, when the connector 10 is coupled to the resonance signal generation circuit 74, the capacitor 32 becomes part of the circuit 74. The capacitor 32 is parallel to the capacitor 34. Thus, the capacitances are added together to lower the operating frequency of the dental generator unit 50.

Alternatively, a capacitor may be present but not operational inside the resonance signal generation circuitry 74. When the handpiece connector 10 is coupled to the generator 50, the capacitor becomes operational. Such a scheme is depicted in FIG. 4C, according to one embodiment.

Before connection, the capacitor 36 is not coupled to the inductor 32 or the capacitor 34 of the resonance circuit. When the handpiece connector 10 is engaged to the generator 50, the resulting capacitance of the circuit increases, due to the parallel configuration of the capacitor 36 with the capacitor 34, again, producing a lower resonant frequency.

By connecting the inductor 30 within the handpiece to the dental generator unit 50, as in FIG. 4A, a base resonant frequency can be generated that will match the resonant frequency of the handpiece/tip.

Further, the frequency can be changed to automatically support a variety of handpieces 14 by introducing or removing capacitance in the handpiece connector 10, such as in FIG. 4B, or from within the resonance signal generation circuit 74, such as in FIG. 4C. In this manner, the same generator 50 can be used with handpiece/tip combinations that operate at different resonant frequencies.

The value of the capacitor 32 that is wired into the handpiece connector 10 may be determined empirically, based on the other circuitry (see FIGS. 7A–7B) and the frequency desired. In one embodiment, the circuit board is configured to produce at the highest resonant frequency when no capacitance is added at the connector 10 (see FIG. 4A).

Footswitch: In addition to automatically supporting multiple handpieces, the ultrasonic dental scaler 100 also supports multiple footswitches or foot pedals. Returning to FIG. 1, a footswitch 44 is shown, coupled to the dental generator unit 50 by a footswitch connector 42.

In one embodiment, the dental generator unit 50 may receive either of two types of footswitches 44 (and associated footswitch connectors 42). The dental generator unit 50 automatically recognizes which footswitch 44 is connected, and adjusts operation of the dental scaler 100 accordingly.

A footswitch 44a, known herein as an on/off footswitch, performs a power-on function. When the on/off footswitch 44a is depressed, the dental generator unit 50 is turned on. When the on/off footswitch 44a is released, the dental generator unit 50 is turned off. No further adjustment of the resonance signal 40 occurs with the footswitch 44a. A potentiometer knob 38 mounted on a panel of the generator unit 50 can adjust the level of power supplied.

A second type of footswitch 44b is a type of power level control footswitch. Recall that power from the dental generator unit 50 is converted to a resonant frequency. Rather than supplying the power to the handpiece 14 corresponding to the set point of the potentiometer 38, the power sent to the handpiece 14 is adjusted using a potentiometer inside the power level control footswitch 44b. In this manner, the power level control footswitch 44b allows the dental professional to control the power level supplied to the resonance signal generation circuit 74.

In FIG. 1, the dental generator unit 50 includes a potentiometer knob 38. In one embodiment, the potentiometer knob 38 is connected to the potentiometer 46, inside the unit 50 (see FIG. 3). The potentiometer knob 38 is a knob that is adjusted, up or down, to control the power sent from the dental generator unit 50 to the handpiece 14.

In one embodiment, where an on/off footswitch 44a is plugged into the unit, the potentiometer knob 38 is operative. Where the power level control footswitch 44b is used, however, the potentiometer knob 38 is inoperative.

In one embodiment, the footswitch connector 42 is a seven-pin connector that engages to the dental generator unit 50. One pin is dedicated as a ground pin. The other pins couple to circuitry of the dental generator unit 50 to activate the circuitry and operate the dental scaling function.

Figure 5:
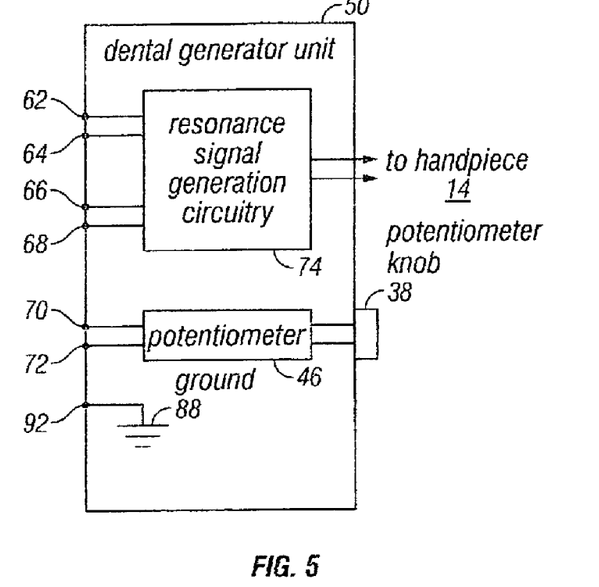
FIG. 5 is a block diagram of the dental generator unit according to one embodiment of the invention.

In FIG. 5, the seven pins 62, 64, 66, 68, 70, 72, and 92 are shown. The resonance signal generation circuitry 74 connects to four of the pins 62, 64, 66, and 68, for connection to the footswitch 44. The potentiometer 46 is connected to the potentiometer knob 38 and, by pins 70 and 72, to the footswitch connector 42.

Figure 6A:
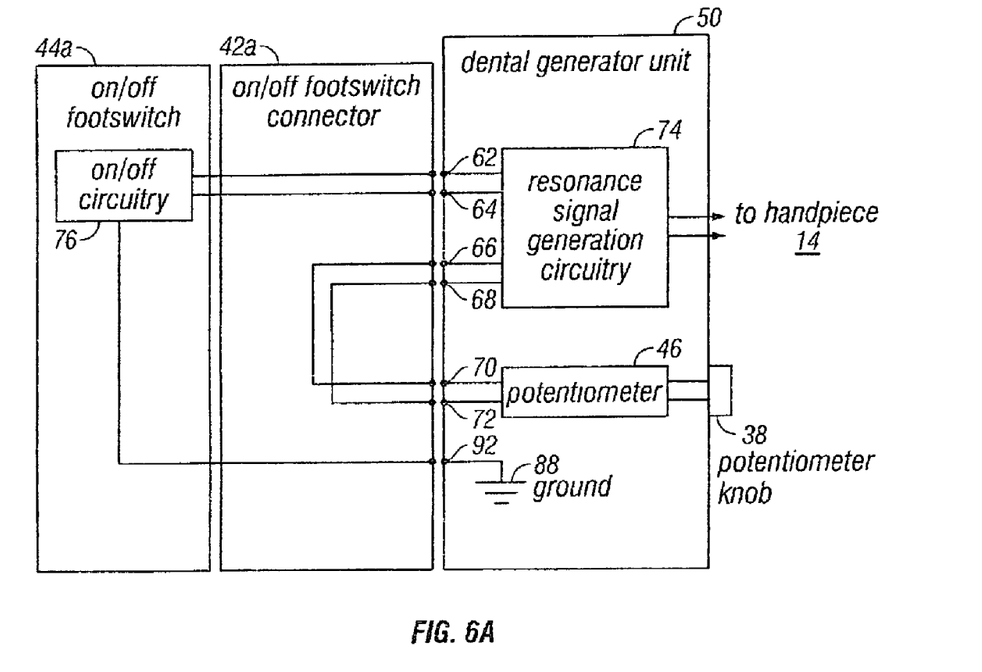
FIGS. 6A and 6B are block diagrams of the on/off and power level control footswitches used by the ultrasonic dental scaler according to one embodiment of the invention.
Figure 6B:
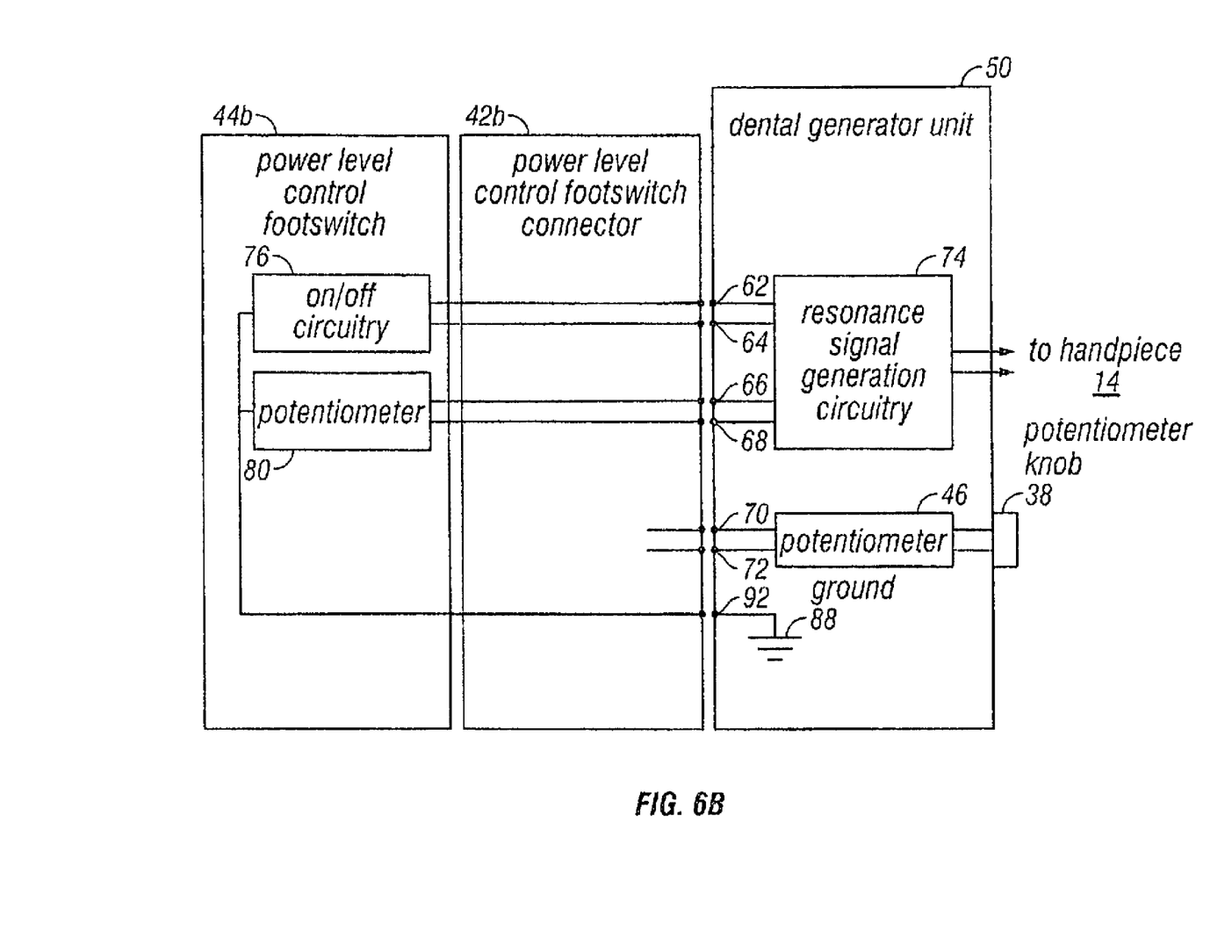

FIGS. 6A and 6B depict the on/off and power level control footswitches, respectively, to be connected to the dental generator unit 50, according to one embodiment. In FIG. 6A, the on/off footswitch connector 42a and the on/off footswitch 44a connect to the dental generation unit 50 at the seven pins (62, 64, 66, 68, 70, 72, and 92).

The on/off footswitch 44a includes on/off circuitry 76, which couples to the dental generator unit 50 by pins 62 and 64. Thus, the on/off circuitry 76 is coupled directly to the resonance signal generation circuitry 74, allowing the on/off footswitch 44a to control power to the dental generator unit 50.

Further, the on/off footswitch connector 42a ties two pairs of connectors together, such as using a pair of wires. When engaged to the dental generator unit 50, pins 66 and 70 are coupled together. Likewise, pins 68 and 72 are coupled together. The configuration couples the potentiometer 46 to the resonance signal generation circuitry 74.

Without the on/off footswitch connector 42a, the signal generation circuitry 74 and the potentiometer 46 remain separated. Adjusting the potentiometer knob 38 has no effect. Once the on/off footswitch connector 42a is engaged, however, the potentiometer 46 may be adjusted to effect the desired power input to the circuitry 74.

In FIG. 6B, a power level control footswitch connector 42b and a power level control footswitch 44b connect to the dental generation unit 50, at the seven pins (62, 64, 66, 68, 70, 72, and 92). As compared to the on/off footswitch connector 42a, the power level control footswitch connector 42b produces different results.

In one embodiment, the power level control footswitch 44b includes on/off circuitry 76, which couples to the dental generator unit 50 by pins 62 and 64. As with the on/off footswitch 44a, the on/off circuitry 76 is coupled directly to the resonance signal generation circuitry 74, allowing the power level control footswitch 44b to control power to the dental generator unit 50.

The power level control footswitch connector 42b includes its own potentiometer 80. The potentiometer 80 is coupled to the resonance signal generation circuitry 74 by pins 66 and 68, as shown in FIG. 6B. This allows the power level control footswitch 44b to adjust both the power sent to the resonance signal generation circuitry 76 and the strength of the power sent.

The power level control footswitch connector 42b includes no connections for connectors 70 and 72. This has the effect of isolating the potentiometer 46 from the resonance signal generation circuitry 74. The potentiometer 80 replaces the potentiometer 46.

Thus, the ultrasonic dental scaler 100 automatically receives at least two different types of footswitches. Further, each footswitch is fully functional as intended. The ultrasonic dental scaler 100 further receives a variety of different handpiece and cable assemblies and automatically adjusts the resonant frequency produced to comply with the frequency requirements and limitations of each.

Programmable Logic Controller: In addition to the handpiece and footswitch features described above, the ultrasonic dental scaler 100 supports a programmable logic controller, in one embodiment. The programmable logic controller is a plug-in connector device, which changes the parameters of the calibration of the dental generator unit 50.

Returning to FIG. 1, a programmable logic controller 82 is depicted, coupling to the dental generator unit 50. Although shown as connecting to the dental generator unit 50 at a distinct point, the programmable logic controller 82 alternatively couples to the unit through one of the other connectors, at the handpiece connector 10 or the footswitch connector 42.

When engaged, the programmable logic controller 82 changes the operation of the dental generator unit 50. In one embodiment, the programmable logic controller 82 changes characteristics, such as the frequency, of the resonance signal 40.

The programmable logic controller 82 modifies the operational behavior of the dental generator unit 50 in other ways as well. For example, the programmable logic controller 82 controls or adjusts the generator frequency range and the power ratio, as examples. Using the programmable logic controller 82, a dental professional may "customize" the ultrasonic dental scaler 100 to suit specific needs.

In one embodiment, a distinct programmable logic controller 82 is used with for each thickness range of tips. In other words, each programmable logic controller 82 limits the maximum power of the resonance signal 40 such that tips associated with the programmable logic controller are used, ensuring that the tips are not broken through excessive power.

In another embodiment, the programmable logic controller 82 expands the range of the potentiometer 46 so that the entire range of the potentiometer is within the safe range of the tip(s), rather than reaching the maximum power supported by the dental generator unit.

Like the handpiece and footswitch circuitry, the programmable logic controller 82 can include passive elements, such as resistors, capacitors, inductors, connecting wires, and so on, in one embodiment. When coupled to the dental generator unit 50, these passive elements change the operation of the underlying circuitry. These passive elements become part of the circuitry much as the passive elements in the handpiece and footswitch circuitry became part of the unit (see FIGS. 4A–4C and 6A–6B).

The programmable logic controller 82 can alternatively or additionally include a read only memory or ROM chip that communicates with the generator unit 50 to receive data concerning the handpiece or handpiece connector and send instructions to the generator unit 50 limiting the maximum power output to match the maximum power accepted by the handpiece.

Figure 7A:
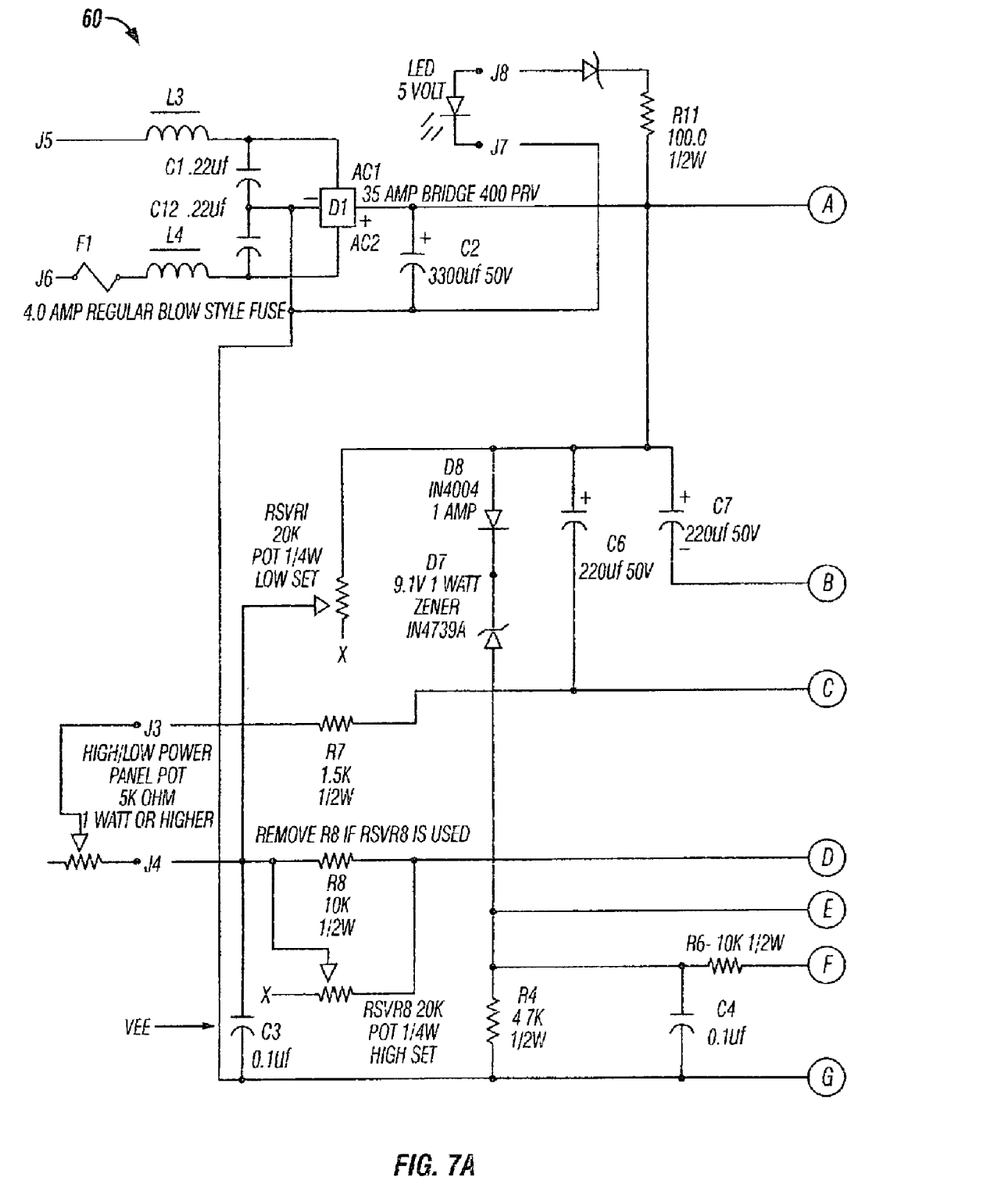
FIGS. 7A and 7B are a schematic circuit diagram of the dental generator unit of FIG. 1 according to one embodiment of the invention.
Figure 7B:
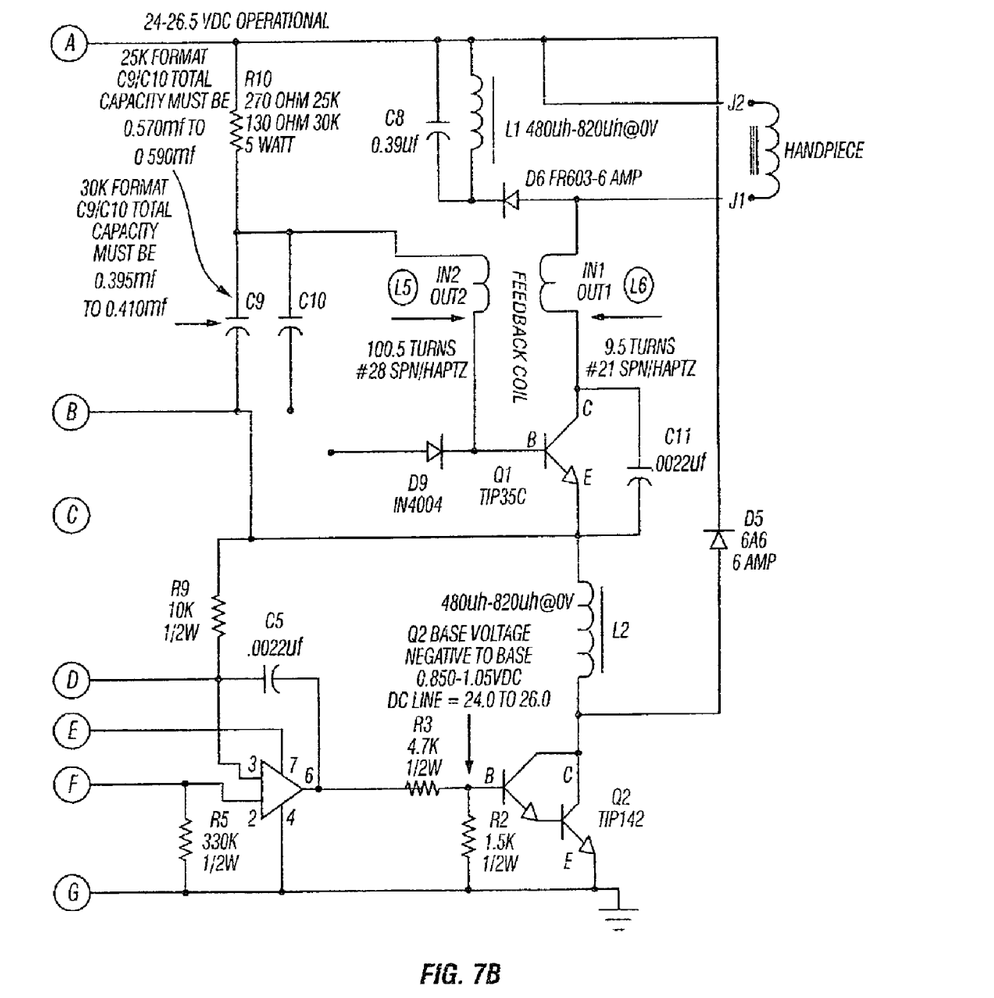

A circuit 60, enclosed in the dental generator unit 50, is depicted in FIGS. 7A–7B, according to one embodiment. The circuit 60 employs one or more of the techniques described above.

Customer Satisfaction: The ultrasonic dental scaler 100 enhances customer satisfaction by simplifying the ordering process. A customer can make a first request for multiple handpieces according to the resonant frequency desired. Since the dental generator unit operates with handpieces that operate at different resonance frequencies, a single dental generator unit can be purchased. Alternatively or additionally, the customer can make a second request for either or both of the footswitches, as each is operable with the dental generator unit. These first and/or second requests can, if desired, be made independently or together in individual, separate or combined orders.

Rather than match handpieces to generators, then generators to footswitches, a supplier of the ultrasonic dental scaler ships a single generator to all customers. The handpiece connector, which includes a capacitor that is associated with a particular resonant frequency, can be paired with the handpiece in advance of customer orders. When orders are received, the likelihood of mistakes is reduced, in some embodiments, due to a much simpler procedure for the supplier.

While the invention has been described with respect to a limited number of embodiments, those skilled in the art will appreciate numerous modifications and variations therefrom. It is intended that the appended claims cover all such modifications and variations as fall within the true spirit and scope of the invention.

What is claimed is:

1. An ultrasonic dental scaler comprising:
   a dental generator unit comprising circuitry to couple with an inductor in a handpiece for producing a base resonance signal;
   a handpiece connector for removably coupling the handpiece to the dental generator unit; and
   a passive circuit element coupled to the circuitry and the inductor via the handpiece connector to adjust a frequency of the base resonance signal to a second frequency matching a resonant frequency of the handpiece.

2. The ultrasonic dental scaler of claim 1, further comprising:
   a first potentiometer in the dental generator unit for adjusting the power level of the resonance signal.

3. The ultrasonic dental scaler of claim 2, further comprising:
   a power level controlling footswitch comprising a second potentiometer; and
   a footswitch connector for removably coupling the footswitch to the dental generator unit, wherein the footswitch connector disables the first potentiometer and couples the second potentiometer in the footswitch to the dental generator unit.

4. The ultrasonic dental scaler of claim 2, further comprising:
   a footswitch connector for removably coupling a simple footswitch to the dental generator unit, wherein the simple footswitch connector enables the first potentiometer.

5. The ultrasonic dental scaler of claim 4, further comprising:

a programmable logic control device for adjusting the frequency of the base resonance signal.

6. The ultrasonic dental scaler of claim 1, wherein the passive circuit element is a capacitor.

7. The ultrasonic dental scaler of claim 6, wherein the capacitor is in the handpiece connector.

8. The ultrasonic dental scaler of claim 6, wherein the capacitor is in the dental generator unit isolated from the circuitry and wherein the handpiece connector includes wiring to couple the capacitor to the circuitry and thereby adjust the frequency of the base resonance signal to the second frequency.

9. An ultrasonic dental scaler comprising:
a dental generator unit comprising:
circuitry for producing a base resonance signal: and
a first potentiometer for adjusting a power level to the circuitry;
a footswitch connectable to the dental generator unit, wherein the footswitch, when engaged with the dental generator unit, selectively sends power to the dental generator unit, wherein the footswitch enables operation of the first potentiometer; and
a second potentiometer within the footswitch;
wherein the first potentiometer is disabled when the footswitch is connected to the dental generator unit.

10. The ultrasonic dental scaler of claim 9, wherein the footswitch comprises a pair of wires such that when the footswitch is engaged with the dental generator unit, the first potentiometer adjusts the power level to the circuitry.

11. An ultrasonic dental scaler comprising:
a footswitch comprising circuitry for sending power to the ultrasonic dental scaler;
signal generation circuitry in the ultrasonic dental scaler;
a first potentiometer separate from the signal generation circuitry; and
a footswitch connector coupled between the footswitch and the ultrasonic dental scaler, wherein the footswitch connector operatively connects the signal generation circuitry in the ultrasonic dental scaler to the first potentiometer.

12. The footswitch of claim 11, wherein the first potentiometer is within the ultrasonic dental scaler.

13. The footswitch of claim 11, wherein the first potentiometer is within the footswitch.

14. An ultrasonic dental scaler comprising:
a footswitch comprising:
circuitry for sending power to the ultrasonic dental scaler; and
a first potentiometer;
a footswitch connector coupled between the footswitch and the ultrasonic dental scaler, wherein the footswitch connector connects circuitry in the ultrasonic dental scaler to a first potentiometer in the footswitch; and
a second potentiometer;
wherein the second potentiometer is disabled when the footswitch is connected to the ultrasonic dental unit.

* * * * *